US009162998B2

(12) United States Patent
Backes et al.

(10) Patent No.: US 9,162,998 B2
(45) Date of Patent: *Oct. 20, 2015

(54) PREPARATION OF 5-HYDROXYMETHYLFURFURAL (HMF) FROM SACCHARIDE SOLUTIONS IN THE PRESENCE OF A SOLVENT HAVING A BOILING POINT GREATER THAN 60° C. AND LESS THAN 200° C. (AT STANDARD PRESSURE, CALLED LOW BOILER FOR SHORT)

(71) Applicant: BASF SE, Ludwigshafen (DE)

(72) Inventors: René Backes, Lampertheim (DE); Benoit Blank, Mannheim (DE); Alois Kindler, Grünstadt (DE); Carmen Feldner, Ludwigshafen (DE)

(73) Assignee: BASF SE (DE)

( * ) Notice: Subject to any disclaimer, the term of this patent is extended or adjusted under 35 U.S.C. 154(b) by 80 days.

This patent is subject to a terminal disclaimer.

(21) Appl. No.: 13/712,056

(22) Filed: Dec. 12, 2012

(65) Prior Publication Data
US 2013/0150597 A1    Jun. 13, 2013

Related U.S. Application Data (60) Provisional application No. 61/569,795, filed on Dec. 13, 2011, provisional application No. 61/684,173, filed on Aug. 17, 2012.

(51) Int. Cl.
C07D 307/46    (2006.01)

(52) U.S. Cl.
CPC .................................. C07D 307/46 (2013.01)

(58) Field of Classification Search
None
See application file for complete search history.

(56) References Cited

U.S. PATENT DOCUMENTS

| | | | |
|---|---|---|---|
| 2,929,823 A | 3/1960 | Garber et al. | |
| 3,201,331 A | 8/1965 | Hunter | |
| 4,400,468 A | 8/1983 | Faber | |
| 4,740,605 A | 4/1988 | Rapp | |
| 2004/0073035 A1 | 4/2004 | Maase et al. | |
| 2009/0270608 A1* | 10/2009 | Zhang et al. | 536/124 |
| 2010/0081798 A1 | 4/2010 | Balensiefer et al. | |
| 2010/0112646 A1 | 5/2010 | Balensiefer et al. | |
| 2011/0275868 A1 | 11/2011 | Prochazka et al. | |
| 2012/0270033 A1 | 10/2012 | Granstrom et al. | |
| 2012/0330035 A1 | 12/2012 | Kindler et al. | |
| 2012/0330039 A1 | 12/2012 | Kindler et al. | |

FOREIGN PATENT DOCUMENTS

| | | |
|---|---|---|
| CN | 101456850 A | 6/2009 |
| CN | 101812039 A | 8/2010 |
| CN | 102399203 A | 4/2012 |
| DE | 3601281 A1 | 7/1987 |
| DE | 102 02 838 A1 | 8/2003 |
| EP | 1834950 A1 | 9/2007 |
| EP | 1834951 A1 | 9/2007 |
| FR | 2663933 A1 | 1/1992 |
| FR | 2664273 A1 | 1/1992 |
| WO | WO-2008090155 A1 | 7/2008 |
| WO | WO-2008090156 A1 | 7/2008 |
| WO | WO-2011/003669 | 1/2011 |
| WO | WO-2012/130880 | 10/2012 |

OTHER PUBLICATIONS

Wei et al. CN 102399203A, Apr. 2012, machine translation.*
Descores et al. FR 2664273 A1, Jan. 10, 1992, machine translation.*
Lewkowski, ARKIVOC 2001 (i) 17-54.*
Glover, Selecting Evaporators for Process Applications, Reprinted from Chemical Engineering Progress, Dec. 2004.*
U.S. Appl. No. 13/711,717, filed Dec. 12, 2012.
U.S. Appl. No. 13/712,056, filed Dec. 12, 2012.
U.S. Appl. No. 13/711,810, filed Dec. 12, 2012.
Chheda, J. et al., "Production of 5-hydroxymethylfurfural and furfural by dehydration of biomass-derived mono-and poly-saccharides", Green Chem., vol. 9, (2007), p. 342-350.
International Search Report for PCT/EP2012/075059, mailing date Jan. 30, 2013.
Kuster, B., "5-Hydroxymethylfurfural (HMF). A Review Focussing on its manufacture", vol. 42, No. 8, (1990), p. 314-321.
van Dam, H.E., et al., "The conversion of Fructose and Glucose in Acidic Media: Formation of Hydroxymethylfurfural", Starch/starke, vol. 38, (1986), pp. 95-101.
Rosatella, A., et al., "5-Hydroxymethylfurfural (HMF) as a Building Block Platform: Biological Properties, Synthesis and Synthetic Applications", Green Chem, vol. 13, (2011), pp. 754-793.

* cited by examiner

*Primary Examiner* — Layla Bland
(74) *Attorney, Agent, or Firm* — Drinker Biddle & Reath LLP (57) ABSTRACT

A process for preparing 5-hydroxymethylfurfural (HMF), which comprises
a) feeding solutions (hereinafter called starting solution) comprising
  one or more saccharides and
  an organic solvent having a boiling point greater than 200° C. (at standard pressure) (called high boiler for short) and
  water,
  and a solvent having a boiling point greater than 60° C. and less than 200° C. (at standard pressure, called low boiler for short) to a reaction vessel,
b) effecting a conversion of hexose to HMF in the reaction vessel in the presence of water vapor with simultaneous distillative removal of the HMF and
c) obtaining, as the distillate, an aqueous, HMF-comprising solution (hereinafter called distillate).

22 Claims, 3 Drawing Sheets

FIGURE 1:

Apparatus composed of thin-film evaporator (Sambay) and device for condensation

FIGURE 2:
Apparatus composed of distillation column and device for condensation with a simple feed

FIGURE 3:

Apparatus composed of distillation column and device for condensation with separate heatable feeds and mixer

US 9,162,998 B2

PREPARATION OF 5-HYDROXYMETHYLFURFURAL (HMF) FROM SACCHARIDE SOLUTIONS IN THE PRESENCE OF A SOLVENT HAVING A BOILING POINT GREATER THAN 60° C. AND LESS THAN 200° C. (AT STANDARD PRESSURE, CALLED LOW BOILER FOR SHORT)

CROSS-REFERENCE TO RELATED APPLICATIONS

This application claims the benefit of U.S. Provisional Application No. 61/569,795, filed Dec. 13, 2011, and U.S. Provisional Application No. 61/684,173, filed Aug. 17, 2012, both of which are incorporated herein by reference.

BACKGROUND OF THE INVENTION

Preparation of 5-hydroxymethylfurfural (HMF) from saccharide solutions in the presence of a solvent having a boiling point greater than 60° C. and less than 200° C. (at standard pressure, called low boiler for short)

DESCRIPTION

The present invention relates to a process for preparing 5-hydroxymethylfurfural (HMF), which comprises
a) feeding solutions (hereinafter called starting solution) comprising
  one or more hexoses or oligomers or polymers formed from hexoses (collectively called saccharides hereinafter) and
  an organic solvent having a boiling point greater than 200° C. (at standard pressure) (called high boiler for short) and
  water,
and a solvent having a boiling point greater than 60° C. and less than 200° C. (at standard pressure, called low boiler for short) to a reaction vessel,
b) effecting a conversion of hexose to HMF in the reaction vessel in the presence of the low boiler with simultaneous distillative removal of the HMF and
c) obtaining, as the distillate, a dilute solution comprising HMF, water and low boilers (hereinafter called distillate).

For chemical syntheses, increasing significance is being gained by compounds which are obtained from renewable raw materials and can be converted easily by chemical reactions to industrially usable compounds.

In this context, 5-hydroxymethylfurfural (HMF) is known, this being preparable by different processes from hexoses or other saccharides. From HMF, for example, 2,5-furandicarboxylic acid is easily obtainable, the latter being suitable as a dicarboxylic acid for preparation of polymers, such as polyesters or polyurethanes, and can replace other dicarboxylic acids from non-renewable raw materials in industrial applications.

HMF is generally prepared by acid-catalyzed dehydration of hexoses such as glucose or fructose. The reaction products obtained are acidic solutions which, as well as the HMF, comprise unconverted starting materials and/or by-products. In the HMF synthesis, there is generally only a partial conversion of the starting materials in order to avoid the formation of by-products. In general, the solutions obtained therefore comprise unconverted starting materials such as hexoses, or oligomers or polymers formed from hexoses. At higher conversions, the amount of by-products increases.

The removal of the HMF from the reaction solution, which comprises starting materials or by-products from the HMF synthesis, is complex and makes it difficult to obtain HMF.

Feroz Kabir Kazi et al. in Chem. Eng. J. 169 (2011), pages 329-338, describe the separation of the HMF from the acidic reaction solution by a complex extraction process using an organic solvent (butanol); a solution of HMF in butanol is obtained.

DE-A 3601281 discloses a chromatographic removal process in which any organic solvents are first removed and the aqueous HMF solution is separated with an ion exchanger column. The HMF fraction obtained is crystallized.

A further method of separating HMF from the reaction solution is the conversion of the HMF to another, more easily removable compound, optionally followed by a reverse conversion to HMF on completion of removal. For instance, HMF, according to Mark Mascal and Edward B. Nikitin in 2008 Angew. Chemie Vol. 47, pages 7924-7926, is converted to the more stable 5-chloromethylfurfural and then back to HMF or derivatives thereof. Alternatively, the ethers of HMF are prepared according to EP-A 1834950, or the esters according to EP-A 1834951, these being directly suitable for further syntheses on completion of removal.

Haru Kawamoto, Shinya Saito et al. describe, in J. Wood Sci. (2007), 53, pages 127-133, the pyrolysis of cellulose to form levoglucosenone, furfural and/or HMF under various conditions, including the supply of water vapor.

FR2663933 and FR2664273 describe how fructose and sucrose are converted to HMF in a melt of acidic salts ($Na_3PO_4$ and $KH_2PO_4$) under the action of superheated steam. A small portion of the HMF is entrained by the steam, but the majority of the HMF is subsequently isolated from the salt melt by means of extraction.

U.S. Pat. No. 4,400,468 discloses the acidic hydrolysis of biomass under the action of water vapor to give sugars, and the direct conversion of the hexose components present in the mixture to HMF. In this case, the HMF formed, however, is not isolated in pure form.

HMF should be present in a form of maximum purity for further syntheses. Aqueous solutions of HMF suitable for further syntheses are particularly those which comprise by-products or residual starting materials in very small amounts at most, if any. Processes known to date for preparing HMF or aqueous solutions thereof with sufficient purity are extremely complex.

CN102399203 and Wei et al. in Green Chem., 2012, 14, pages 1220-1226 disclose a distillative process for simultaneous preparation and isolation of HMF by degradation of fructose and glucose in ionic liquids. The process comprises the addition of a saccharide to an ionic liquid based on imidazolium derivatives, preferably with long alkyl side chains (e.g. 1-methyl-3-octylimidazolium chloride) in the presence of a cocatalyst and of a stripping medium at 100 to 500 Pa, a reaction temperature of 120-180° C. and a reaction time of 10 to 60 minutes. The stripping medium is nitrogen, another inert gas, carbon dioxide, a C1-C8 alkane, acetone or methyl isobutyl ketone.

The cobalt catalyst used is a metal salt or metal oxide which serves for stabilization of the HMF formed, but also serves as a catalyst for the isomerization of glucose to fructose. Such an isomerization with metal salts is already known from the literature (Glucose-isomerization with Chromium-salts—Science 2007, 316, 1597-1600; Angew. Chem. Int. Ed. 2008, 47, 9345-9348; Chem. Eur. J. 2011, 17, 5281-5288; Glucose-isomerization with rare-earth metals—J. Mol. Cat. A, 2012, 356, 158-164; HMF from Glucose with lanthanides—Green Chem., 2010, 12, 321-325; Conversion of Cellulose to Furans with metal salts—J. Mol. Catal. A, 2012, 357, 11-18; Sn-Beta Zeolites—ACS Catal. 2011, 1, 408-410).

The use of ionic liquids, especially of substituted imidazolium chloride derivatives, for the synthesis of HMF from fructose and glucose is well known in the literature. However, not only is the isolation of the HMF formed from the ionic liquid very complex—usually, the IL is extracted with an organic solvent, and the reaction in ILs also proceeds much more slowly in the presence of water and the saccharide is therefore converted in very substantially anhydrous IL in all cases. The latter has to be dewatered in a complex manner prior to further use (e.g. Biores. Tech. 2011, 102, 4179-4183).

The adverse effect of water in the reaction medium in the conversion of sugars, especially fructose and glucose, to HMF has been adequately described in the literature (e.g. Carbohydr. Res. 1977, 54, 177-183; Science 2007, 136, 1597-1600). As is well known to those skilled in the art, water firstly slows the dehydration reaction of the sugars, and also promotes the rehydration and splitting of the HMF formed to formic acid and levulinic acid (for the postulated mechanism of the reaction see Science 2006, 312, 1933-1937). As shown in example 1, the reaction proceeds much more slowly with rising water content and gives lower yields of HMF.

DETAILED DESCRIPTION OF THE INVENTION

The object of the present invention was therefore an industrial scale process with which HMF can be prepared in a very simple and effective manner, HMF is at the same time obtained in very substantially pure form, and HMF is therefore separated directly and very substantially completely from converted starting materials or by-products.

In industrial scale processes, the conversion is to be performed within an industrially and economically advantageous temperature and pressure range with high conversion and high space-time yield. More particularly, the use of commercially available aqueous saccharide solutions in different concentrations, as opposed to crystalline saccharides, is of high significance. Furthermore, the feedstocks should make minimum demands on the apparatuses and the procedure, and enable simple purification and isolation of the product of value. The use of a gas as a stripping medium in a reaction regime under reduced pressure is difficult to implement on the industrial scale since a high pump output is required in order that the desired vacuum can be maintained. In the case of the industrial scale use of organic solvents as stripping media, the high costs and complex recovery thereof are disadvantageous. In the case of preparation of HMF, moreover, short residence times at high temperatures are highly advantageous due to the instability of the product. Especially a rapid removal of the HMF formed from the reaction solution enables higher yields. A significant factor in industrial scale processes is the complexity of the process, such that, for example, one-pot processes are preferable for different reasons. A particularly preferred process variant is reactive distillation, in which the target product is formed in a one-pot process and is simultaneously separated from the reaction solution.

Accordingly, the process defined at the outset has been found.

In the process according to the invention, HMF is prepared in the presence of a solvent having a boiling point greater than 60° C. and less than 200° C. (at standard pressure, called low boiler for short) and is separated directly from by-products and unconverted starting materials of the HMF synthesis. In contrast to the prior art, this process can be performed on the industrial scale.

Process Step a)

In process step a), solutions (hereinafter called starting solution) comprising
one or more hexoses or oligomers or polymers formed from hexoses (collectively called saccharides hereinafter) and
an organic solvent having a boiling point greater than 200° C. (at standard pressure) (called high boiler for short) and
water,
and a solvent having a boiling point greater than 60° C. and less than 200° C. (at standard pressure, called low boiler for short) are fed to a reaction vessel.

The saccharide comprises hexoses, or oligomers or polymers formed from hexoses. The hexoses are preferably fructose, glucose or mixtures of fructose and glucose. Particular preference is given to fructose or mixtures of fructose with glucose. The hexose is most preferably fructose.

The starting solution may also comprise by-products or starting materials from the preparation of the saccharides. For example, saccharides can be obtained by degradation of polymers such as cellulose or starch. Therefore, the starting solution may still comprise residual amounts of such polymers or the oligomeric degradation products thereof.

The starting solution preferably comprises 1 to 60% by weight of saccharide, more preferably 10 to 50% by weight of saccharide, based on the total weight of the starting solution.

The starting solution preferably comprises less than 10% by weight, especially less than 5% by weight and more preferably less than 1% by weight of by-products or starting materials from the preparation of saccharides (based on the total weight of the starting solution). More particularly, the starting solution is essentially free of by-products and starting materials from the preparation of saccharides.

In an alternative embodiment, the starting solution may also comprise metal chlorides or metal nitrates of the general formula MXn as isomerization salts, where M is a metal, X is chlorine or nitrate and n is an integer from 1 to 4. These isomerization salts are preferably present in the starting solution when the saccharide in the starting solution is glucose or a saccharide comprising glucose units, for example sucrose. The use of isomerization salts has already been described in the literature (Science 2007, 316, 1597-1600, Carbohydr. Pol. 2012, 90, 792-798, Chem. Eur. J. 2011, 17, 5281-5288, Green Chem. 2009, 11, 1746-1749). Preference is given to using metal chlorides or metal nitrates selected from the group of $CrCl_2$, $CrCl_3$, $AlCl_3$, $FeCl_2$, $FeCl_3$, $CuCl$, $CuCl_2$, $CuBr$, $VCl_3$, $MoCl_3$, $PdCl_2$, $PtCl_2$, $RuCl_3$, $RhCl_3$, $Ni(NO_3)_2$, $Co(NO_3)_2$, $Cr(NO_3)_3$, $SnCl_4$. Very particular preference is given to $CrCl_2$ and $CrCl_3$.

The starting solution further comprises an organic solvent having a boiling point greater than 200° C. (at standard pressure), especially greater than 250° C. (called high boiler for short hereinafter).

Useful high boilers include hydrophilic solvents; these may be protic, hydrophilic organic solvents, for example alcohols, or aprotic hydrophilic solvents, for example ethers or ketones, such as dimethyl sulfoxide. Also useful are ionic liquids, high-boiling oils, for example paraffins, and high-boiling esters, for example Hexamoll DINCH (diisononyl 1,2-cyclohexane-dicarboxylate). Further possible high boilers are: 1,3-dimethylpropyleneurea (DMPU), tri-n-octylphosphine oxide (TOPO), hexamethylphosphoramide (HMP), 3-methyl-2-oxazolidone, 2-oxazolidone, o-dihydroxybenzene, catechol, N,N-dibutylurea and dibutyl sulfone.

High boilers preferred in the context of this invention are polyethers and ionic liquids.

Polyethers

The polyethers preferably have a melting point less than 60° C., especially less than 30° C. (at standard pressure, 1 bar). Particularly preferred polyethers are liquid at 20° C. (standard pressure).

The polyethers comprise at least two ether groups. The polyethers preferably comprise at least 3, especially at least 4 and more preferably at least 6 ether groups. In general, they comprise not more than 40 and especially not more than 30 ether groups, more preferably not more than 20 ether groups.

In a particular embodiment, the polyethers do not comprise any heteroatoms apart from oxygen in the form of ether groups and optionally hydroxyl groups.

More particularly, the polyethers are aliphatic polyethers, particularly preferred polyethers being polyalkylene glycols, where the terminal hydroxyl groups may be etherified with alkyl groups, especially C1-C4-alkyl groups.

The alkylene groups of the polyalkylene glycols may, for example, be C2 to 010 and especially C2 to C4 alkylene groups, such as ethylene, propylene or butylene groups. The polyalkylene glycols may also comprise various alkylene groups, for example in the form of blocks.

Very particular preference is therefore given to poly-C2- to -C4-alkylene glycols, especially polyethylene glycol, the terminal hydroxyl groups of which may optionally be etherified with alkyl groups; the number of repeat alkylene ether groups corresponds to the above number of ether groups, the number of repeat alkylene ether groups being especially 4 to 30, more preferably 6 to 20. The terminal hydroxyl groups of the polyalkylene glycols may be etherified with alkyl groups, especially C1 to C4 alkyl groups.

Ionic Liquid (IL)

Ionic liquids refer in the context of the present application to organic salts which are liquid even at temperatures below 180° C. The ionic liquids preferably have a melting point of less than 150° C., more preferably less than 120° C., especially less than 100° C.

Ionic liquids which are present in the liquid state even at room temperature are described, for example, by K. N. Marsh et al., Fluid Phase Equilibria 219 (2004), 93-98 and J. G. Huddleston et al., Green Chemistry 2001, 3, 156-164.

Ionic liquids suitable for use in the process according to the invention are described in WO 2008/090155 (page 4, line 38 to page 37, line 31) and WO 2008/090156 (page 7, line 1 to page 39, line 37), reference being made thereto.

In the ionic liquid, cations and anions are present. Within the ionic liquid, a proton or an alkyl radical can be transferred from the cation to the anion, resulting in two uncharged molecules. In the ionic liquid used in accordance with the invention, there may thus be an equilibrium of anions, cations and uncharged molecules formed therefrom.

Preferred ionic liquids are combinations of nitrogen-containing cation components (such as imidazolium derivatives) and halogen ions as anions.

Suitable compounds suitable for formation of the cation of ionic liquids are described, for example, in DE 102 02 838 A1 ([0030] to [0073]). These compounds preferably comprise at least one heteroatom, for example 1 to 10 heteroatoms, which are preferably selected from nitrogen, oxygen, phosphorus and sulfur atoms. Preference is given to compounds which comprise at least one nitrogen atom and optionally additionally at least one further heteroatom other than nitrogen. Preference is given to compounds comprising at least one nitrogen atom, more preferably 1 to 10 nitrogen atoms, especially 1 to 5 nitrogen atoms, even more preferably 1 to 3 nitrogen atoms and especially 1 or 2 nitrogen atoms. The latter nitrogen compounds may comprise further heteroatoms such as oxygen, sulfur or phosphorus atoms.

Preference is given to those compounds which comprise at least one five- to six-membered heterocycle, especially a five-membered heterocycle, which has at least one nitrogen atom and optionally an oxygen or sulfur atom. Particular preference is given to those compounds which comprise at least one five- to six-membered heterocycle which has one, two or three nitrogen atoms and one sulfur or one oxygen atom, very particular preference to those having two nitrogen atoms. Preference is further given to aromatic heterocycles.

Preferred cations are unsubstituted or substituted imidazolium ions. Particularly suitable imidazolium ions are 1-methylimidazolium, 1-ethylimidazolium, 1-(1-propyl)imidazolium, 1-(1-allyl)imidazolium, 1-(1-butyl)imidazolium, 1-(1-octyl)imidazolium, 1-(1-dodecyl)imidazolium, 1-(1-tetradecyl)imidazolium, 1-(1-hexadecyl)imidazolium, 1,3-dimethylimidazolium, 1,3-diethylimidazolium, 1-ethyl-3-methylimidazolium, 1-(1-butyl)-3-methylimidazolium, 1-(1-butyl)-3-ethylimidazolium, 1-(1-hexyl)-3-methylimidazolium, 1-(1-hexyl)-3-ethylimidazolium, 1-(1-hexyl)-3-butylimidazolium, 1-(1-octyl)-3-methylimidazolium, 1-(1-octyl)-3-ethylimidazolium, 1-(1-octyl)-3-butylimidazolium, 1-(1-dodecyl)-3-methylimidazolium, 1-(1-dodecyl)-3-ethylimidazolium, 1-(1-dodecyl)-3-butylimidazolium, 1-(1-dodecyl)-3-octylimidazolium, 1-(1-tetradecyl)-3-methylimidazolium, 1-(1-tetradecyl)-3-ethylimidazolium, 1-(1-tetradecyl)-3-butylimidazolium, 1-(1-tetradecyl)-3-octylimidazolium, 1-(1-hexadecyl)-3-methylimidazolium, 1-(1-hexadecyl)-3-ethylimidazolium, 1-(1-hexadecyl)-3-butylimidazolium, 1-(1-hexadecyl)-3-octylimidazolium, 1,2-dimethylimidazolium, 1,2,3-trimethylimidazolium, 1-ethyl-2,3-dimethylimidazolium, 1-(1-butyl)-2,3-dimethylimidazolium, 1-(1-hexyl)-2,3-dimethylimidazolium, 1-(1-octyl)-2,3-dimethylimidazolium, 1,4-dimethylimidazolium, 1,3,4-trimethylimidazolium, 1,4-dimethyl-3-ethylimidazolium, 3-methylimidazolium, 3-ethylimidazolium, 3-n-propylimidazolium, 3-n-butylimidazolium, 1,4-dimethyl-3-octylimidazolium, 1,4,5-trimethylimidazolium, 1,3,4,5-tetramethylimidazolium, 1,4,5-trimethyl-3-ethylimidazolium, 1,4,5-trimethyl-3-butylimidazolium, 1,4,5-trimethyl-3-octylimidazolium, 1-prop-1-en-3-yl-3-methylimidazolium and 1-prop-1-en-3-yl-3-butylimidazolium. Specifically suitable imidazolium ions (IVe) are 1,3-diethylimidazolium, 1-ethyl-3-methylimidazolium, 1-(n-butyl)-3-methylimidazolium.

The anion of the ionic liquid is selected, for example, from 1) anions of the formulae: $F^-$, $Cl^-$, $Br^-$, $I^-$, $BF_4^-$, $PF_6^-$, $CF_3SO_3^-$, $(CF_3SO_3)_2N^-$, $CF_3CO_2^-$, $CCl_3CO_2^-$, $CN^-$, $SCN^-$, $OCN^-$.

2) anions of the formulae: $SO_4^{2-}$, $HSO_4^-$, $SO_3^{2-}$, $HSO_3^-$, $R^cOSO_3^-$, $R^cSO_3^-$.
3) anions of the formulae: $PO_4^{3-}$, $HPO_4^{2-}$, $H_2PO_4^-$, $R^cPO_4^{2-}$, $HR^cPO_4^-$, $R^cR^dPO_4^-$.
4) anions of the formulae: $R^cHPO_3^-$, $R^cR^dPO_2$, $R^cR^dPO_3^-$.
5) anions of the formulae: $PO_3^{3-}$, $HPO_3^{2-}$, $H_2PO_3^-$, $R^cPO_3^{2-}$, $R^cHPO_3^-$, $R^cR^dPO_3^-$.
6) anions of the formulae: $R^cR^dPO_2^-$, $R^cHPO_2^-$, $R^cR^dPO^-$, $R^cHPO^-$.
7) anions of the formula $R^cCOO^-$.
8) anions of the formulae: $BO_3^{3-}$, $HBO_3^{2-}$, $H_2BO_3^-$, $R^cR^dBO_3^-$, $R^cHBO_3^-$, $R^cBO_3^{2-}$, $B(OR^c)(OR^d)(OR^e)(ORf)^-$, $B(HSO_4)_4^-$, $B(R^cSO_4)_4^-$.
9) anions of the formulae: $R^cBO_2^{2-}$, $R^cR^dBO^-$.
10) anions of the formulae: $HCO_3^-$, $CO_3^{2-}$, $R^cCO_3^-$
11) anions of the formulae: $SiO_4^{4-}$, $HSiO_4^{3-}$, $H_2SiO_4^{2-}$, $H_3SiO_4^-$, $R^cSiO_4^{3-}$, $R^cR^dSiO_4^{2-}$, $R^cR^dR^eSiO_4^-$, $HR^cSiO_4^{2-}$, $H_2R^cSiO_4^-$, $HR^cR^dSiO_4^-$
12) anions of the formulae: $R^cSiO_3^{3-}$, $R^cR^dSiO_2^{2-}$, $R^cR^dR^eSiO_2^-$, RcRdReSiO$^-$, $R^cR^dR^eSiO_2^-$, $R^cR^dSiO_3^{2-}$.
13) anions of the formulae:

14) anions of the formulae:

15) anions of the formula $R^cO^-$.
16) anions of the formulae $HS^-$, $[Sv]^{2-}$, $[HSv^-]$, $[R^cS]^-$, where v is a positive integer from 2 to 10. The $R^c$, $R^d$, $R^e$ and $R^f$ radicals are preferably each independently
hydrogen;
unsubstituted or substituted alkyl, preferably unsubstituted or substituted C1-C30-alkyl, more preferably unsubstituted or substituted C1-C18-alkyl, which may be interrupted by at least one heteroatom or a heteroatom-containing group;
unsubstituted or substituted aryl, preferably unsubstituted or substituted C6-C14-aryl, more preferably unsubstituted or substituted C6-C10-aryl;
unsubstituted or substituted cycloalkyl, preferably unsubstituted or substituted C5-C12-cycloalkyl;
unsubstituted or substituted heterocycloalkyl, preferably unsubstituted or substituted heterocycloalkyl having 5 or 6 ring atoms, where the ring, as well as carbon ring atoms, has 1, 2 or 3 heteroatoms or heteroatom-containing groups;
unsubstituted or substituted heteroaryl, preferably unsubstituted or substituted heteroaryl having 5 to 10 ring atoms, where the ring, as well as carbon ring atoms, has 1, 2 or 3 heteroatoms or heteroatom-containing groups selected from oxygen, nitrogen, sulfur and $NR^a$; where any two of these radicals in anions having a plurality of $R^c$ to $R^f$ radicals, together with the part of the anion to which they are bonded, may be at least one saturated, unsaturated or aromatic ring or a ring system having 1 to 12 carbon atoms, where the ring or ring system may have 1 to 5 nonadjacent heteroatoms or heteroatom-containing groups preferably selected from oxygen, nitrogen, sulfur and NRa, and where the ring or ring system is unsubstituted or may be substituted.

Preferred anions are Cl$^-$, Br$^-$, formate, acetate, propionate, butyrate, lactate, saccharinate, carbonate, hydrogencarbonate, sulfate, sulfite, C1-C4-alkylsulfates, methanesulfonate, tosylate, trifluoroacetate, C1-C4-dialkylphosphates and hydrogensulfate.

Particularly preferred anions are Cl$^-$, Br$^-$, HCOO$^-$, $CH_3COO^{31}$, $CH_3CH_2COO^-$, carbonate, hydrogencarbonate, sulfate, sulfite, tosylate, $CH_3SO_3^-$ or $CH_3OSO_3$.

More particularly, the anions are selected from Cl$^-$ and $CH_3SO_3^-$.

Suitable ionic liquids for use in the process according to the invention are commercially available, for example, under the Basionic® brand name from BASF SE.

Advantageous ionic liquids for use in the process according to the invention are imidazolium chlorides or imidazolium methanesulfonates or mixtures thereof.

Further advantageous ionic liquids for use in the process according to the invention are, for example, 1-ethyl-3-methylimidazolium chloride (EMIM Cl, Basionic ST 80), 1-ethyl-3-methylimidazolium methanesulfonate (EMIM $CH_3SO_3$, Basionic ST 35), 1-butyl-3-methylimidazolium chloride (BMIM Cl, Basionic ST 70), 1-butyl-3-methylimidazolium methanesulfonate (BMIM $CH_3SO_3$, Basionic ST 78), methylimidazolium chloride (HMIM Cl, Basionic AC 75), methylimidazolium hydrogensulfate (HMIM $HSO_4$ Basionic AC 39), 1-ethyl-3-methylimidazolium hydrogensulfate (EMIM $HSO_4$ Basionic AC 25), 1-butyl-3-methylimidazolium hydrogensulfate (BMIM $HSO_4$ Basionic AC 28) 1-ethyl-3-methylimidazolium acetate (EMIM acetate, Basionic BC 01), 1-butyl-3-methylimidazolium acetate (BMIM acetate, Basionic BC 02). Particular preference is given to 1-ethyl-3-methylimidazolium chloride, 1-butyl-3-methylimidazolium chloride, methylimidazolium chloride, 1-ethyl-3-methylimidazolium methanesulfonate, 1-butyl-3-methylimidazolium methanesulfonate and mixtures thereof.

Very particular preference is given to 1-ethyl-3-methylimidazolium chloride (EMIM Cl, Basionic ST 80), 1-butyl-3-methylimidazolium chloride (BMIM Cl, Basionic ST 70) and 1-ethyl-3-methylimidazolium methanesulfonate (EMIM $CH_3SO_3$, Basionic ST 35).

The starting solution comprises, as well as the high boiler, at least one further solvent. The further solvent is especially water. This may also include mixtures of water with hydrophilic organic solvents having a boiling point less than 200° C. (called low boilers) in which the saccharide used should preferably be soluble.

The further solvent is more preferably water. The starting solution is therefore more preferably an aqueous solution.

In a particular embodiment, the starting solution comprises exclusively water and the high boiler as solvents.

The starting solution comprises the high boiler, especially the polyether or the ionic liquid, preferably in amounts of 5 to 90% by weight, especially of 30 to 80% by weight, more preferably of 40 to 80% by weight, based on the total weight of the starting solution.

The water content of the starting solution is preferably less than 60% by weight, especially less than 50% by weight and more preferably less than 40% by weight, based on the total weight of the starting solution.

The starting solution preferably further comprises a catalyst. The catalyst catalyzes the conversion of the saccharide to HMF. Suitable catalysts are acids. Useful acids include heterogeneous acids which are dispersed in the starting solution, or homogeneous acids which are dissolved in the starting solution. Useful homogeneous acids include any desired inorganic or organic acids. Particular preference is given to using homogeneous protic acids. Examples include para-toluenesulfonic acid, methanesulfonic acid ($MeOSO_3H$), oxalic acid, sulfuric acid, hydrochloric acid or phosphoric acid.

If the high boiler used is an ionic liquid or DMSO, the use of a catalyst is not absolutely necessary, especially in the case of halide-containing ILs, for example EMIMCl and BMIMCl. However, the use of a catalyst accelerates the reaction and hence reduces the residence time in process step b). Thus, in the case of use of ionic liquids or DMSO as high boilers, preference is given to using a catalyst.

If a polyether, especially polyethylene glycol, is used as the high boiler, the use of a catalyst is absolutely necessary.

The starting solution comprises the acid preferably in amounts of 0.1 to 10 mol %, more preferably of 0.1 to 5 mol % (based on the saccharide).

Preferred starting solutions comprise, for example,
1 to 40% by weight of saccharide
5 to 90% by weight of high boiler, preferably polyether or ionic liquid
1 to 50% by weight of water
0.1 to 10 mol % of acid (based on the saccharide)
0 to 10% by weight of other constituents, for example by-products from the synthesis of the saccharide,
based on the total weight of the solution.

Particularly preferred starting solutions comprise, for example,
5 to 30% by weight of saccharide
30 to 80% by weight of high boiler, preferably polyether or ionic liquid
10 to 50% by weight of water
0.1 to 5 mol % of acid (based on the saccharide)
0 to 5% by weight of other constituents, for example by-products from the synthesis of the saccharide,
based on the total weight of the solution.

The starting solution can be prepared here in various ways. In one embodiment, the components of the starting solution are supplied to a reaction vessel and premixed therein. In that case, this starting solution is supplied to process step b). In this case, this starting solution, in a particular embodiment, can also be preheated beforehand to a temperature of 150-200° C.

In an alternative embodiment, the starting solution is prepared by the following steps:
a1) The saccharide and water are present in a reaction vessel.
a2) A further reaction vessel is initially charged with the high boiler and preferably the catalyst.
a3) Immediately prior to process step b), the components are mixed, preferably in a mixing chamber.

In a further alternative embodiment, as well as the high boiler and preferably the catalyst, a metal chloride or metal nitrate may also be initially charged in process step a2). Preference is given to initially charging a metal chloride or metal nitrate when the saccharide used in process step a1) is glucose or the saccharide used comprises glucose units, for example sucrose.

"Immediately prior to process step b)" means that the period from commencement of the mixing time in process step a) until the entry of the mixture into the reaction vessel, preferably an evaporator, is at most 5 minutes, more preferably at most one minute.

In an alternative embodiment, the mixed starting solution can additionally be partly vaporized by an instantaneous pressure gradient (transition from standard pressure to a vacuum by means of a pressure regulator) and converted to the gas phase (called "flashing").

In a further alternative embodiment, the solutions of steps a1 and a2 in the two reaction vessels can be preheated to a temperature between 150 and 200° C., for example by means of a heat exchanger, separately from one another prior to the mixing.

In this case, the aqueous starting solution is already in a supercritical state and may, in a further alternative embodiment, be vaporized particularly efficiently by an instantaneous pressure gradient (transition from elevated pressure to a vacuum by means of a pressure regulator) and a relatively large proportion of water can be converted to the gas phase (called "flashing").

In the case of high boilers which are solid or else very viscous at room temperature, heating of the reservoir vessels may be necessary in order that they are melted beforehand and are pumpable.

The above-described starting solution and the solvent having a boiling point greater than 60° C. and less than 200° C. (at standard pressure, called low boilers for short) are supplied to a reaction vessel.

Process Step b)

In process step b), the starting solution is converted to HMF in conjunction with a distillation which is known per se, in the presence of a solvent having a boiling point greater than 60° C. and less than 200° C. (at standard pressure, called low boiler for short). For this purpose, the starting solution is contacted with the low boiler in the reaction vessel.

Preferred low boilers are water vapor, alcohols, for example methanol, ethanol, 2-butanol, mono-, di- and polyethers, such as ethylene glycol dimethyl ether, diethylene glycol monomethyl ether, triethylene glycol, ketones such as 2-butanone or methyl isobutyl ketone, esters such as butyl acetate, and aromatics such as toluene or xylene. Preference is given to polar protic low boilers which enable a good interaction with HMF. The low boilers used are more preferably water vapor, methanol and 2-butanol. Very particular preference is given to water vapor.

The treatment of the starting solution with the low boiler is effected preferably under reduced pressure, a useful pressure being especially from 10 to 200 mbar. The pressure in the reaction vessel is preferably 10 to 100 mbar, more preferably 20 to 80 mbar.

The treatment of the starting solution with the low boiler is effected preferably at a temperature of the starting solution of 100 to 250° C., more preferably of 140 to 250° C. and more preferably of 160 to 220° C. and most preferably 170 to 220° C.

If the high boiler used is a polyethylene glycol, the starting solution is treated with the low boiler preferably at a temperature of 160 to 220° C.

If the high boiler used is an ionic liquid, the starting solution is treated with the low boiler preferably at a temperature of 180 to 220° C.

If the low boiler used is water vapor, the treatment of the starting solution with water vapor is effected preferably at a temperature of 140 to 220° C., more preferably at 160 to 220° C. and most preferably at 180 to 220° C. At these temperatures, the treatment can be effected with an industrially viable but minimal amount of water vapor. By increasing the amount of water vapor, the separating performance of the reactive distillation can be increased or kept constant at the same or a low temperature, but the use of an elevated amount of water vapor is less preferred for industrial reasons, since a high level of complexity is necessary to keep the pressure constant, a higher cooling performance on the distillate side is needed, and the steam costs rise.

In a further alternative embodiment, no low boiler is supplied to the reaction vessel. In this embodiment, the low boiler takes the form of water vapor in the reaction vessel from the water in the starting solution.

The process according to the invention is preferably operated continuously.

For this purpose, the starting solution and the low boiler are supplied continuously to the reaction vessel, and the product obtained, or distillate, is removed continuously.

The volume flow rates depend on the size, the reactor performance and the separation performance of the reaction vessel selected.

In a preferred embodiment, the ratio of the amount of low boiler supplied to the amount of the starting solution supplied is within a range from 0.2 to 4 weight units of low boiler to 1 weight unit of starting solution, more preferably in the range from 0.3 to 2 weight units of low boiler to 1 weight unit of starting solution, and especially 0.3 to 1.5 weight units of low boiler to 1 weight unit of starting solution.

Suitable reaction vessels are customary evaporators which are designed for the supply of starting solution and low boiler and especially for the above-described continuous procedure. The evaporator used is preferably an evaporator with short residence time in the range of seconds to minutes (2 seconds to 10 minutes). Advantageously, low thermal stress on the dehydration products formed is thus achieved. The residence time has a strong influence on the yield of HMF, since the distillation yield of HMF declines significantly as a result of an increased residence time in the event that conversion is already complete.

The residence time is therefore preferably 1 to 120 seconds, more preferably 1 to 60 seconds, most preferably 5 to 30 seconds.

A suitable evaporator is in principle an apparatus customary for that purpose, which in the simplest case comprises a vessel or tubes with heatable walls as heat transfer surfaces. The evaporator may suitably be supplied with heat from the outside through the walls, for example with steam. The temperature in the evaporator is preferably within a range from 100 to 300° C., more preferably within a range from 150° C. to 250° C. The pressure in the evaporator is preferably at most 100 mbar. The pressure in the evaporator is more preferably within a range from 10 mbar to 100 mbar, especially 10 mbar to 80 mbar.

In one embodiment, the evaporator used is a thin-film evaporator in which the starting solution in the evaporator is present as a liquid film.

Particular preference is given to vertical thin-film evaporators; such vertical thin-film evaporators are known by device names such as "Luwa" or especially "Sambay" from Buss or Sulzer. The thin-film evaporator can be used with or without a rotating wiper blade.

The preferred vertical thin-film evaporators are ultimately a vertical tube with internal devices for distribution and mixing of the starting solution, and external devices for heating of the tube wall. The starting solution is preferably supplied in the upper part of the thin-film evaporator and distributed as a film on to the heated pipe wall. The low boiler can be supplied to the evaporator, preferably to the thin-film evaporator, together with the starting solution or at any other point in the evaporator. The starting solution and the low boiler may be conducted within the evaporator in the same direction (cocurrent) or in opposite directions (countercurrent).

The low boiler is preferably conducted in countercurrent to the starting solution. For this purpose, the starting solution is supplied especially in the upper part of the evaporator and the steam in the lower part of the evaporator.

The low boiler and the volatile constituents of the starting solution are preferably discharged via a separator at the top of the evaporator and condensed (distillate).

The nonvolatile constituents pass through the evaporator and are removed as liquid bottom product.

BRIEF DESCRIPTION OF THE FIGURES

Figure 1:
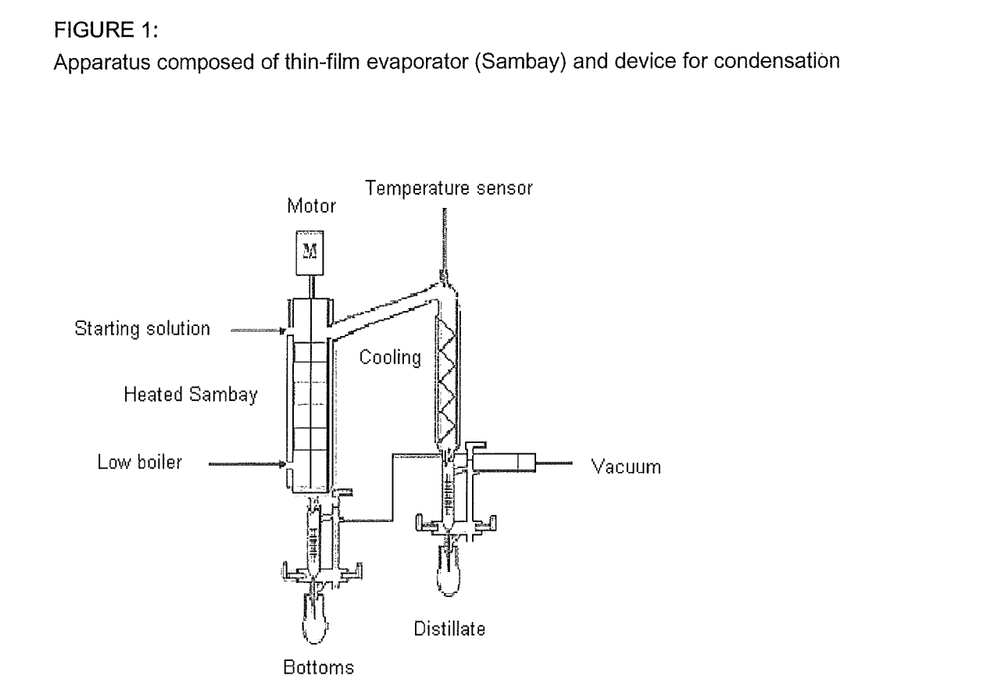
FIG. 1 shows an apparatus composed of thin-film evaporator and device for condensation.

FIG. 1 (FIG. 1) shows a corresponding apparatus composed of thin-film evaporator (Sambay) and device for condensation.

In an alternative embodiment, conversion and removal are accomplished using a distillation column, preferably a stripping column. The stripping column may consist of a vertical tube with external heating and a plurality of separation stages for the establishment of the liquid/vapor equilibrium. The feed is preferably to the top of the stripping column.

In a further alternative embodiment, a droplet separator (demister) is arranged above the distillation column. This prevents droplet entrainment (a sign of nonestablishment of equilibrium and simultaneously fluid-dynamic/flow-related overloading).

The starting solution is preferably supplied to the top of the distillation column. The low boiler can be supplied to the evaporator together with the starting solution or at any other point in the evaporator. The starting solution and the low boiler can be conducted within the evaporator in the same direction (cocurrent) or opposite directions (countercurrent).

The low boiler is preferably conducted in countercurrent to the starting solution. For this purpose, the starting solution is especially supplied in the upper part of the evaporator and the low boiler in the lower part of the evaporator.

The low boiler and the volatile constituents of the starting solution are preferably discharged via a separator at the top of the evaporator and condensed (distillate).

The nonvolatile constituents pass through the evaporator and are removed as liquid bottom product.

Figure 2:
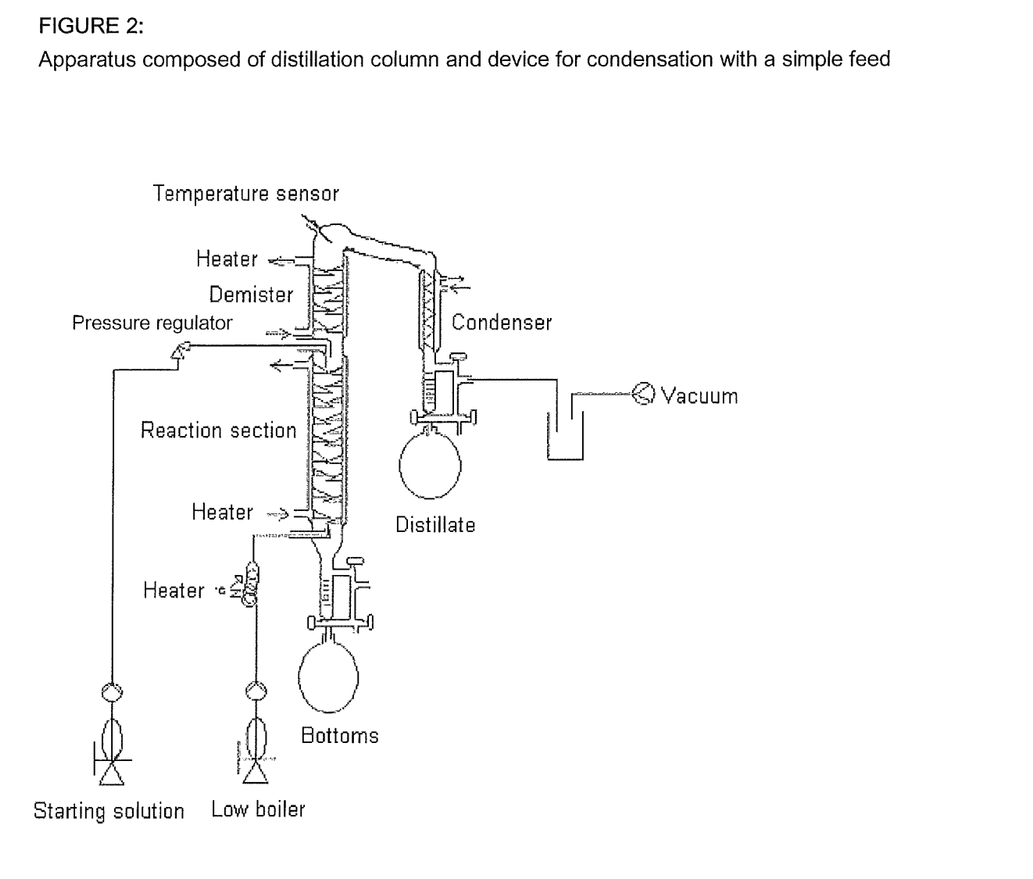
FIG. 2 shows an apparatus composed of a distillation column and device for condensation with a simple feed.

FIG. 2 (FIG. 2) shows a corresponding apparatus composed of distillation column and device for condensation with a simple feed.

Figure 3:
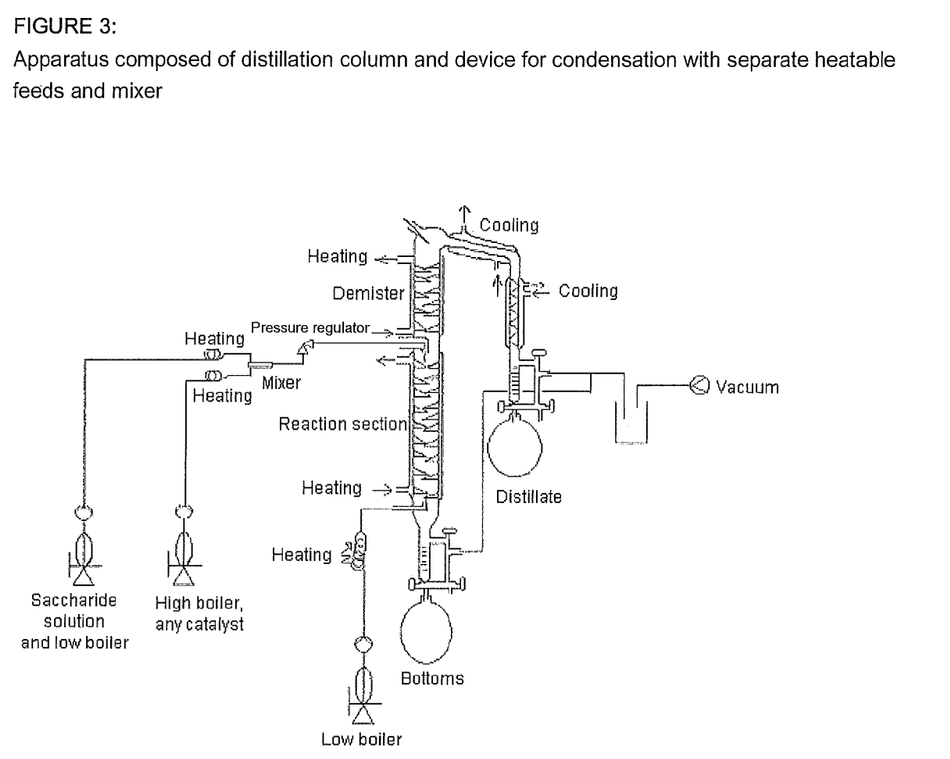
FIG. 3 shows an apparatus composed of a distillation column and device for condensation with separate heatable feeds and mixer.

FIG. 3 (FIG. 3) shows a corresponding apparatus composed of distillation column and device for condensation with separate heatable feeds and mixer.

The reaction in process step b) can, if desired, be performed such that only partial conversion of the saccharide to HMF or full conversion of the saccharide to HMF is effected. In the case of partial conversion, unconverted saccharide can be converted again; in the case of full conversion, there may be increased formation of by-products, especially what are called humins, i.e. oligomers of HMF.

Preferably at least 60%, especially at least 80% and, in a particular embodiment, at least 90% of the saccharide used is converted.

Process Step c)

The distillate obtained is a dilute, HMF-comprising solution. The distillate comprises the HMF formed in the conversion and water, and the low boiler from the distillation. The distillate preferably comprises the HMF formed in the conversion and water from the reaction and distillation.

The distillate comprises especially more than 60%, especially more than 80%, of the HMF obtained overall in the conversion.

The distillate comprises especially at least 3% by weight of HMF, more preferably at least 4% by weight of HMF and most preferably at least 6% by weight of HMF, based on the total weight of the distillate.

In addition, the distillate may also comprise high boilers. In the case of use of polyethers or ionic liquids as high boilers, the distillate comprises only very small amounts of high boilers, if any; the content of polyethers or ionic liquids in the distillate is then especially less than 5% by weight, preferably less than 2% by weight and more preferably less than 1 or less than 0.5% by weight, based on the total weight of the distillate.

By-products which form in the conversion of the saccharide to HMF are especially humins (oligomers of HMF). The humins are obtained in the process according to the invention essentially not in the distillate but in the bottoms (see FIG. 1).

The distillate therefore comprises only very small amounts of humins, if any; the content of humins in the distillate is generally less than 2% by weight, especially less than 0.5% by weight and more preferably less than 0.1% by weight, based on the total weight of the distillate. The distillate is clear and has a pale yellow or orange color (according to the HMF content).

In addition, the distillate comprises only small amounts of unconverted saccharide, if any; unconverted saccharide is present predominantly in the bottoms.

The content of unconverted saccharide in the distillate is generally less than 5% by weight, especially less than 2% by weight and more preferably less than 1% by weight, based on the total weight of the distillate.

It is an advantage of the process according to the invention that by-products of the HMF synthesis, polyethers or ionic liquids as high boilers and unconverted saccharide are obtained essentially in the bottoms.

HMF is obtained in the preparation process according to the invention directly as distillate with high purity. The process according to the invention is therefore a simple and effective process for preparation of HMF and simultaneous removal of HMF from by-products and unconverted starting materials.

The distillate is suitable for chemical syntheses in which HMF is used as a starting material. More particularly, the distillate is suitable for chemical syntheses in which the HMF starting material is desired or required in high purity. An example given here is that of the use of the product solution for preparation of 2,5-furandicarboxylic acid or of 2,5-bis(hydroxymethyl)furan.

EXAMPLES

Example 1

Batch Experiments for HMF Preparation in IL with Variable Water Content

The experiments were performed batchwise in a glass round-bottom flask with reflux condenser, mechanical stirrer and oil bath heating.

The starting solutions comprised: fructose (20 g), high boiler (100 g), p-toluenesulfonic acid (1 mol % based on fructose) and variable amounts of water.

The high boilers used were:
PEG-600: a polyethylene glycol having a molecular weight of 600
BMIMCl: 1-butyl-3-methylimidazolium chloride (BMIM Cl, Basionic ST 70)

Performance of the Batch Reactions:

All substances were initially charged in the round-bottom flask, heated rapidly to 100° C. and, after attainment of the target temperature, the timing was started and samples were taken from the reaction vessel at regular intervals for reaction monitoring.

The composition was determined by means of HPLC.

The conversions of fructose reported are calculated from the residual amounts of fructose in the samples analyzed; fructose was converted to HMF and to by-products (humins). The HMF yield is the percentage of HMF formed based on the fructose content in the starting solution.

TABLE 1

Batch experiments for HMF preparation in IL with variable water content

| Solvent | Water content | Time | Conversion (%) | Yield (%) |
|---|---|---|---|---|
| BMIMCl | none | <10 min | 93% | 84% |
| BMIMCl | approx. 10% by wt. | 1 h | 98% | 74% |
| BMIMCl | approx. 20% by wt. | 2 h | 99% | 74% |
| PEG-600 | none | 8 h | 97% | 43% |
| PEG-600 | 2% by weight | 8 h (18 h) | 94% (98%) | 33% (43%) |

Example 2

In Situ Dehydration of Fructose and Isolation of HMF by Means of Steam Distillation Starting Solution The starting solutions were obtained by mixing pure substances.

The starting solutions comprised fructose, high boiler, acid and water (see table).

The high boilers used were:
DMSO: dimethyl sulfoxide
PEG-600: a polyethylene glycol having a molecular weight of 600
Tetraglyme: tetraethylene glycol dimethyl ether The acids used were:
H2SO4: sulfuric acid
p-TSA: para-toluenesulfonic acid
MSA: methanesulfonic acid
Oxalic acid Performance of Steam Distillation The steam distillation was performed in the apparatus according to FIG. 1. The apparatus consisted of a glass Sambay which is operated in countercurrent mode.

The starting solution was supplied at the top and flashed into vacuum by means of a pressure regulator, and the water vapor as the low boiler in the lower third.

The composition of the starting solution for various high boilers and the selected temperatures and pressures are listed in the table.

The temperature reported is that of the heating medium at the outer pipe wall, which corresponds in a good approximation to that of the liquid film of the starting solution on the inner pipe wall.

The experiments were performed continuously; after each new temperature and pressure adjustment, attainment of a steady state was awaited.

The composition was determined by means of HPLC.

The reported conversions of fructose are calculated from the residual amounts of fructose in the bottoms and distillate; fructose was converted to HMF and to by-products (humins). The reported catalytic amounts of acid are based on fructose. The HMF yield is the molar percentage of the HMF in the distillate or in the bottoms, based on the fructose content in the starting solution.

$$HMF \text{ yield: } \frac{m(HMF)/M/HMF)}{m(Fru)/M(Fru)} * 100$$

The temperature specified is that of the heating medium at the outer pipe wall, which corresponds in a good approximation to that of the liquid film of the starting solution at the inner pipe wall.

The experiments were performed continuously; after each new temperature and pressure adjustment, attainment of a steady state was awaited.

The composition was determined by means of HPLC.

The HMF yield is the percentage of HMF in the distillate or in the bottoms, based on the HMF content in the starting solution.

The distillation separation performance is calculated from percentage of HMF in the distillate/percentage of HMF in the bottoms*100.

The fructose recovery is calculated from percentage of fructose in the bottoms/percentage of fructose in the starting solution*100 and is supposed to show that, under these conditions, fructose is not converted and is recovered for the most part in the bottoms.

TABLE 2

Continuous experiments for in situ dehydration of fructose and isolation of HMF

| High boiler | High boiler conc. [% by wt.] | Fructose conc. [% by wt.] | Acid | Amount of acid [mol %, based on mol of fructose] | Temperature [° C.] | Pressure [mbar] | Fructose [% by wt.] in the Distillate | Fructose [% by wt.] in the Bottoms | HMF [% by wt.] in the Distillate | HMF [% by wt.] in the Bottoms | Conversion of fructose [%] | HMF yield [%] Distillate | HMF yield [%] Bottoms |
|---|---|---|---|---|---|---|---|---|---|---|---|---|---|
| tetraglyme | 50 | 10 | oxalic acid | 18 | 160 | 180 | 0.01 | 0.00 | 0.44 | 0.0 | 99.7 | 18.6 | 0.0 |
| DMSO[1] | 90 | 10 | H$_2$SO$_4$ | 0.9 | 160 | 180 | 0.00 | 0.00 | 0.90 | 0.00 | 100.0 | 17.21 | 0.01 |
| DMSO | 90 | 10 | H$_2$SO$_4$ | 0.01 | 110 | 380 | 0.00 | 5.43 | 0.05 | 2.94 | 72.1 | 1.0 | 21.6 |
| PEG-600 | 49 | 24 | MSA | 0.6 | 160 | 25 | 0.17 | 5.73 | 1.73 | 0.22 | 80.9 | 19.1 | 1.0 |
| PEG-600 | 49 | 24 | MSA | 1.0 | 160 | 30 | 0.16 | 0.13 | 1.87 | 0.26 | 98.5 | 19.9 | 1.0 |
| PEG-600 | 49 | 24 | p-TSA | 1.0 | 160 | 30 | 0.03 | 0.07 | 2.12 | 0.39 | 99.6 | 22.2 | 0 |
| PEG-600 | 49 | 24 | oxalic acid | 1.0 | 160 | 30 | 0.17 | 12.72 | 0.40 | 0.31 | 65.7 | 4.0 | 1.2 |

[1]with DMSO as the added solvent, no bottoms were obtained at this temperature with these pressure settings; the entire amount of HMF, DMSO and water is in the distillate.

Example 3

Isolation of HMF from HMF/High Boiler Solutions with Different Low Boilers

Starting Solution

The starting solutions were obtained by mixing pure substances.

The starting solutions comprised HMF (10% by weight), fructose (10% by weight), water (20% by weight) and PEG-600 (60% by weight) based on the total weight of the starting solution. No conversion of fructose to HMF takes place in this solution since no acid has been added.

The fructose was added only to show that it is distilled over into the distillate only in a very small proportion.

Performance of the Distillation

The distillation was performed in the apparatus according to FIG. 1. The apparatus consists of a glass Sambay which is operated in countercurrent mode.

The starting solution was supplied at the top and flashed into vacuum by means of a pressure regulator, and the low boiler in the lower third. The low boiler is heated to 125° C. by means of electrical heating and decompressed by means of a pressure regulator and introduced into the distillation column.

TABLE 3

Results of the isolation of HMF from HMF/high boiler solutions with different low boilers

| High boiler | Low boiler | HMF yield (%) in the distillate | HMF yield (%) in the bottoms | Fructose content in the distillate (% by wt.) | Distillation separation performance HMF distillate/bottoms |
|---|---|---|---|---|---|
| PEG-600 | H$_2$O | 82.3 | 7.6 | 0.06 | 91.5 |
| PEG-600 | no low boiler | 12.1 | 82.7 | 0.12 | 12.8 |
| PEG-600 | 2-BuOH | 43.2 | 49.7 | 0.07 | 46.5 |
| PEG-600 | EGDME | 29.5 | 53.9 | 0.09 | 35.4 |
| PEG-600 | MiBK | 51.2 | 54.5 | 0.23 | 48.4 |
| PEG-600 | Bu—Ac | 18.1 | 66.9 | 0.16 | 21.3 |
| PEG-600 | toluene | 31.6 | 57.78 | 0.15 | 35.4 |

Example 4

In Situ Dehydration of Fructose and Isolation of HMF in a Stripping Column

Starting Solution

The starting solutions were obtained by mixing pure substances.

The starting solutions comprised fructose (20% by weight), high boiler (see table), acid (1 mol % based on fructose) and water (20% by weight), based on the total weight of the starting solution.

The high boilers used were:
PEG-600: a polyethylene glycol having a molecular weight of 600

The composition was determined by means of HPLC.

The reported conversions of fructose are calculated from the residual amounts of fructose in the bottoms and distillate; fructose was converted to HMF and to by-products (humins). The reported catalytic amounts of acid are based on fructose. The HMF yield is the percentage of HMF in the distillate or in the bottoms, based on the fructose content in the starting solution.

The distillation separation performance is calculated from the percentage of HMF in the distillate/percentage of HMF in the bottoms*100

TABLE 4

Continuous experiments for in situ dehydration of fructose and isolation of HMF

| Entry | High boiler | Starting solution flow rate (g/min) | Distillation temp. (° C.) | Distillation pressure (mbar) | Low boiler flow rate (g/min) | Low boiler | Low boiler/ starting solution ratio | HMF conc. in distillate (% by wt.) | Fructose conc. in distillate (% by wt.) | HMF conc. in bottoms (% by wt.) | Fructose conc. in bottoms (% by wt.) |
|---|---|---|---|---|---|---|---|---|---|---|---|
| 1 | EMImCl | 2.1 | 140 | 27 | 2.3 | $H_2O$ | 1.1 | 0.72 | 0.00 | 0.67 | 19.10 |
| 2 | EMImCl | 2.1 | 160 | 33 | 2.3 | $H_2O$ | 1.1 | 1.53 | 0.00 | 1.61 | 0 |
| 3 | EMImCl | 2.1 | 180 | 32 | 2.3 | $H_2O$ | 1.1 | 2.88 | 0.00 | 4.09 | 4.09 |
| 4 | EMImCl | 2.4 | 200 | 34 | 2.4 | $H_2O$ | 1.0 | 6.05 | 0.00 | 2.95 | 0.00 |
| 5 | EMImCl | 2.6 | 220 | 35 | 2.5 | $H_2O$ | 1.0 | 8.10 | 0.00 | 1.14 | 0.00 |
| 6 | EMImCl | 2.9 | 180 | 41 | 5.9 | $H_2O$ | 2.0 | 1.53 | 0.00 | 1.06 | 4.72 |
| 7 | EMImCl | 2.7 | 220 | 81 | 2.5 | $H_2O$ | 0.9 | 8.33 | 0.00 | 1.94 | 0.00 |
| 8 | EMImCl | 2.8 | 220 | 35 | 1.5 | 2-butanol | 0.6 | 7.72 | 0.00 | 4.13 | 0.00 |
| 9 | EMImCl | 1.3 | 180 | 28 | 1.0 | $H_2O$ | 1.0 | 4.35 | 0.00 | 5.52 | 2.26 |
| 10 | EMImCl | 1.2 | 180 | 27 | 3.0 | $H_2O$ | 2.5 | 2.79 | 0.00 | 1.56 | 0.87 |
| 11 | EMImCl | 2.5 | 180 | 44 | 2.3 | methanol | 0.9 | 2.39 | 0.00 | 9.49 | 5.22 |
| 12 | EMImCl | 2.6 | 220 | 45 | 2.3 | methanol | 0.9 | 7.80 | 0.00 | 1.80 | 0.13 |
| 13 | PEG-600 | 1.2 | 140 | 27 | 2.5 | $H_2O$ | 2.1 | 0.66 | 0.00 | 0.84 | 3.51 |
| 14 | PEG-600 | 1.1 | 160 | 27 | 2.6 | $H_2O$ | 2.3 | 1.54 | 0.00 | 0.89 | 0.83 |
| 15 | PEG-600 | 1.3 | 180 | 29 | 2.5 | $H_2O$ | 2.0 | 2.44 | 0.01 | 0.63 | 0.29 |
| 16 | PEG-600 | 1.1 | 200 | 34 | 2.4 | $H_2O$ | 2.3 | 2.55 | 0.01 | 0.13 | 0.18 |
| 17 | PEG-600 | 1.2 | 220 | 35 | 2.7 | $H_2O$ | 2.2 | 2.60 | 0.03 | 0.03 | 0.02 |

EMImCl: 1-ethyl-3-methylimidazolium chloride (EMIM Cl, Basionic ST 80)

The acid used was para-toluenesulfonic acid.

Performance of the Reactive Distillation

The reactive distillation was performed in the apparatus according to FIG. 2. The apparatus consists of a two-part thermostatted glass Vigreux column with a reaction section (below) and a a demister (above the feed of the starting solution). The apparatus is operated in countercurrent mode and the starting solution is supplied via a single feed and flashed into vacuum by means of a pressure regulator.

The starting solution was supplied between demister and reaction section, and the low boiler in the lower third of the column.

The composition of the starting solution for various high boilers and the temperatures and pressures selected are listed in the table.

The temperature reported is that of the heating medium at the outer column wall, which corresponds in a good approximation to that of the liquid of the starting solution at the inner column wall.

The experiments were performed continuously; after each new temperature and pressure setting, attainment of a steady state was awaited.

| Entry | Overall fructose conversion (%) | HMF yield in distillate (%) | HMF yield in bottoms (%) | Overall HMF select. (%) | Distillation separation performance for HMF dist./bottoms |
|---|---|---|---|---|---|
| 1 | 17.8 | 5.5 | 4.1 | 53.9 | 57.1 |
| 2 | 100.0 | 12.1 | 8.8 | 20.9 | 57.8 |
| 3 | 86.1 | 25.3 | 19.9 | 52.5 | 56.0 |
| 4 | 100.0 | 50.6 | 13.4 | 64.1 | 79.1 |
| 5 | 100.0 | 62.6 | 5.5 | 68.1 | 92.0 |
| 6 | 67.8 | 16.8 | 10.3 | 40.0 | 62.0 |
| 7 | 100.0 | 62.9 | 11.7 | 74.6 | 84.3 |
| 8 | 100.0 | 51.3 | 16.1 | 67.4 | 76.1 |
| 9 | 92.8 | 36.0 | 24.9 | 65.6 | 59.1 |
| 10 | 94.5 | 46.9 | 14.0 | 64.4 | 77.1 |
| 11 | 82.6 | 19.4 | 45.0 | 78.0 | 30.1 |
| 12 | 99.7 | 58.1 | 6.8 | 65.1 | 89.5 |
| 13 | 81.5 | 10.1 | 6.3 | 20.2 | 61.7 |
| 14 | 96.3 | 25.9 | 5.7 | 32.8 | 81.9 |
| 15 | 98.8 | 38.2 | 3.4 | 42.1 | 91.8 |
| 16 | 99.2 | 44.0 | 0.8 | 45.2 | 98.2 |
| 17 | 99.6 | 42.6 | 0.2 | 42.9 | 99.6 |

Explanations:

Entries 1-5: Variation of temperature of 140° C.-220° C. with EMIMCl under otherwise identical conditions. The distillation separation performance remains constant at approx. 50% up to 180° C. and then rises rapidly up to 92% at 220° C. It is thus possible to show clearly that the process optimum is at 220° C. in the case of ILs such as EMIMCl.

Entries 3 & 6 and 9 & 10: Increase in the steam rate under otherwise identical conditions. Shows a slight improvement in distillation performance.

Entries 5 & 7: Variation of vacuum. In the case of poorer vacuum from 30 to 80 mbar, the distillation performance falls by 8%.

Entries 5, 8, 12: Use of different low boilers. The same overall selectivity of the reaction is obtained with respect to HMF, but clear differences are found in distillation performance in the sequence of H2O>MeOH>2-BuOH.

Entries 13-17: Use of PEG-600 at different temperatures. The optimum is at 200° C., where the highest HMF selectivity is obtained with high distillation performance. However, at the high temperatures, slight entrainment of sugar into the distillate can be observed, which does not occur in the case of ILs.

Example 5

In Situ Dehydration of Fructose and Isolation of HMF in a Stripping Column with Separate Feeds Starting Solutions The starting solutions were obtained by mixing pure substances.

Feed 1 is the saccharide solution and comprises fructose (40-70% by weight) and water.

Performance of the Reactive Distillation

The reactive distillation was performed in the apparatus according to FIG. 3. The apparatus consists of a two-part thermostatted glass Vigreux column with a reaction section (below) and a demister (above the feed of the starting solution). The apparatus is operated in countercurrent mode and the starting solution is obtained by mixing possibly preheated feed 1 and feed 2, and is flashed into vacuum by means of a pressure regulator.

The starting solution was supplied between demister and reaction section, and the low boiler in the lower third of the column.

The temperature reported is that of the heating medium at the outer column wall, which corresponds in a good approximation to that of the liquid of the starting solution at the inner column wall.

The experiments were performed continuously; after each new temperature and pressure setting, attainment of a steady state was awaited.

The composition was determined by means of HPLC.

The reported conversions of fructose are calculated from the residual amounts of fructose in the bottoms and distillate; fructose was converted to HMF and to by-products (humins). The reported catalytic amounts of acid are based on fructose. The HMF yield is the percentage of HMF in the distillate or in the bottoms, based on the fructose content in the starting solution.

The distillation separation performance is calculated from the percentage of HMF in the distillate/percentage of HMF in the bottoms*100

TABLE 5

Continuous experiments for in situ dehydration of fructose and isolation of HMF with separate feeds

| Entry | Fructose conc. in feed 1 (% by wt.) | Preheater temp. (° C.) | Feed 1 flow rate (g/min) | Feed 2 flow rate (g/min) | Amount of acid (mol %) | Distillation temp. (° C.) | Distillation pressure (mbar) | Feed 3 flow rate (g/min) | Low boiler | Ratio of feed 2/feed 1 |
|---|---|---|---|---|---|---|---|---|---|---|
| 1 | 40 | 180 | 1.3 | 1.2 | 0.9 | 200 | 17 | 2.4 | H$_2$O | 0.9 |
| 2 | 40 | 180 | 1.3 | 1.1 | 0.8 | 220 | 25 | 2.4 | H$_2$O | 0.8 |
| 3 | 40 | 180 | 2.5 | 2.2 | 0.8 | 220 | 32 | 2.4 | H$_2$O | 0.9 |
| 4 | 70 | 180 | 1.5 | 1.1 | 0.7 | 220 | 27 | 2.4 | H$_2$O | 0.8 |
| 5 | 70 | 180 | 1.5 | 1 | 0.8 | 180 | 22 | 2.4 | H$_2$O | 0.9 |
| 6 | 40 | 25 | 2.5 | 2.3 | 0.8 | 220 | 18 | 2.4 | H$_2$O | 0.9 |
| 7 | 40 | 180 | 1.3 | 1.4 | 1.0 | 220 | 35 | 1.9 | MeOH | 1.0 |
| 8 | 40 | 180 | 1.3 | 1.2 | 1.0 | 220 | 18 | 2.3 | EtOAc | 1.0 |
| 9$^a$ | 40 | 180 | 1.3 | 1.4 | 1.0 | 220 | 28 | 2.4 | H$_2$O | 1.0 |

| Entry | Ratio of feed 3/feeds 1&2 | HMF conc. in distillate (% by wt.) | Fructose conc. in distillate (% by wt.) | HMF conc. in bottoms (% by wt.) | Fructose conc. in bottoms (% by wt.) | Overall fructose conversion (%) | HMF yield in distillate (%) | HMF yield in bottoms (%) | Overall HMF selectivity (%) | Distillation separation performance for HMF-dist./bottoms |
|---|---|---|---|---|---|---|---|---|---|---|
| 1 | 0.9 | 7.23 | 0 | 1.67 | 0 | 100 | 65.9 | 5.9 | 71.8 | 91.8 |
| 2 | 1 | 7.21 | 0 | 0.66 | 0 | 100 | 69.8 | 2.4 | 72.2 | 96.7 |
| 3 | 0.5 | 10.52 | 0 | 1.05 | 0 | 100 | 70.9 | 3.6 | 74.5 | 95.2 |
| 4 | 0.9 | 10.32 | 0.00 | 2.27 | 0.00 | 100.0 | 51.1 | 4.1 | 55.2 | 92.6 |
| 5 | 0.9 | 7.9 | 0.0 | 5.68 | 2.91 | 94.9 | 33.8 | 14.3 | 50.8 | 70.2 |
| 6 | 0.5 | 7.41 | 0.00 | 3.88 | 0.62 | 98.2 | 42.8 | 16.1 | 60.0 | 72.6 |
| 7 | 0.7 | 6.58 | 0.00 | 1.01 | 0.00 | 100.0 | 58.5 | 4.3 | 60.6 | 93.0 |
| 8 | 0.9 | 17.89 | 0.00 | 1.76 | 0.00 | 100.0 | 54.1 | 6.8 | 60.9 | 88.8 |
| 9$^a$ | 0.9 | 7.25 | 0.00 | 0.38 | 0.13 | 99.6 | 69.7 | 1.6 | 71.5 | 97.8 |

$^a$in the high boiler solution, EMIM CH$_3$SO$_3$ rather than EMIM Cl was used

Feed 2 is the high boiler solution and comprises the high boiler (EMIMCl—95% by weight), para-toluenesulfonic acid (0.44% by weight) and water (4.5% by weight) based on the total weight of the starting solution.

Feed 3 is the low boiler (water, methanol-MeOH or ethyl acetate-EtOAc).

Explanations:

Entries 1 & 2: The increase in the reaction/distillation temperature achieves a better distillation separation performance, with equal overall selectivity of the reaction.

Entries 2 & 3: A reduction in the amount of low boiler is economically and industrially viable and, for the same overall selectivity and distillation separation performance, gives high HMF contents in the distillate of approx. 10% by weight.

Entries 2 & 4: If a higher concentration of fructose in feed 1 is used, the total water content in the system falls and a poorer selectivity of the reaction is obtained because the HMF formed cannot be removed rapidly enough from the reaction medium.

Entries 4 & 5: A reduction in the reaction temperature to 180° C., even in the case of high fructose contents in feed 1, leads to a poorer distillation separation performance and only to a partial conversion of the fructose.

Entries 3 & 6: If feeds 1 & 2 are not heated, a poorer distillation separation performance and a lower overall selectivity of the reaction are found. This is probably because, as a result of heating of the aqueous saccharide solution, the water is already in a supercritical state and, as a result of the instantaneous decompression, vaporizes much better into the vacuum and thus entrains the HMF formed with it (better flash).

Entries 7 & 8: The low boilers used may also be methanol and ethyl acetate, but slightly poorer distillation separation performances and overall selectivities of the reaction compared to water are obtained. With ethyl acetate, a biphasic distillate is obtained, in which the main proportion of the HMF is in the aqueous phase (the yield reported is based on the overall distillate).

Entry 9: The reaction can be performed with equal yields also with EMIM $CH_3SO_3$.

Example 6

In Situ Dehydration of Glucose or Glucose/Fructose Mixtures and Isolation of HMF in a Stripping Column with Separate Feeds Starting Solutions The starting solutions were obtained by mixing pure substances.

Feed 1 is the saccharide solution and comprises glucose (40% by weight) or glucose/fructose (ratio 58:42—40% by weight total sugar) and water.

Feed 2 is the high boiler solution and comprises the high boiler (EMIMCl—92.95% by weight), $CrCl_3$ (1.72% by weight), para-toluenesulfonic acid (0.42% by weight) and water (4.91% by weight), based on the total weight of the starting solution.

Feed 3 is the low boiler (water).

Performance of the Reactive Distillation

The reactive distillation was performed in the apparatus according to FIG. 3. The apparatus consists of a two-part thermostatted glass Vigreux column with a reaction section (below) and a demister (above the feed of the starting solution). The apparatus is operated in countercurrent mode and the starting solution is obtained by mixing possibly preheated feed 1 and feed 2, and is flashed into vacuum by means of a pressure regulator.

The starting solution was supplied between demister and reaction section, and the low boiler in the lower third of the column.

The temperature reported is that of the heating medium at the outer column wall, which corresponds in a good approximation to that of the liquid of the starting solution at the inner column wall.

The experiments were performed continuously; after each new temperature and pressure setting, attainment of a steady state was awaited.

The composition was determined by means of HPLC.

The reported conversions of total sugar are calculated from the residual amounts of glucose and fructose in the bottoms and distillate; glucose and fructose were converted to HMF and to by-products (humins). The reported catalytic amounts of acid are based on total sugar. The HMF yield is the percentage of HMF in the distillate or in the bottoms, based on the total sugar content in the starting solution.

The distillation separation performance is calculated from the percentage of HMF in the distillate/percentage of HMF in the bottoms*100

TABLE 6

Continuous experiments for in situ dehydration of glucose or glucose/fructose mixtures and isolation of HMF with separate feeds.

| Entry | Feed | Preheater temp. (° C.) | Feed 1 flow rate (g/min) | Feed 2 flow rate (g/min) | Amount of acid (mol %) | Distillation temp. (° C.) | Distillation pressure (mbar) | Feed 3 flow rate (g/min) | Low boiler |
|---|---|---|---|---|---|---|---|---|---|
| 1 | glucose | 180 | 1.3 | 1.3 | 0.8 | 220 | 27 | 2.4 | $H_2O$ |
| 2 | glucose | 180 | 1.3 | 1.3 | 0.8 | 220 | 33 | 1.3 | $H_2O$ |
| 3 | glucose | 180 | 1.3 | 1.2 | 0.8 | 180 | 37 | 2.2 | $H_2O$ |
| 4 | Glu/Fru (58:42) | 180 | 1.3 | 1.3 | 0.8 | 220 | 37 | 2.3 | $H_2O$ |
| 5 | Glu/Fru (58:42) | 180 | 1.3 | 1.3 | 0.8 | 220 | 35 | 1.3 | $H_2O$ |
| 6[a] | glucose | 180 | 1.3 | 1.4 | 1.0 | 200 | 22 | 2.4 | $H_2O$ |

| Entry | Ratio of feed 2/feed 1 | Ratio of feed 3/feeds 1&2 | HMF yield in distillate (%) | Sugar yield in distillate (%) | HMF yield in bottoms (%) | Sugar yield in bottoms (%) | Overall sugar conversion (%) | Overall HMF select. (%) | Overall HMF yield (%) | Distillation separation performance for HMF dist./bottoms |
|---|---|---|---|---|---|---|---|---|---|---|
| 1 | 0.9 | 0.9 | 51.8 | 0.0 | 0.4 | 0.4 | 99.6 | 52.4 | 52.2 | 99.2 |
| 2 | 1.0 | 0.5 | 47.6 | 0.0 | 2.7 | 0.6 | 99.4 | 50.6 | 50.3 | 94.4 |
| 3 | 0.9 | 0.9 | 19.7 | 0.0 | 34.3 | 8.9 | 91.1 | 59.3 | 54.0 | 36.9 |
| 4 | 1.0 | 0.9 | 51.7 | 0.0 | 0.5 | 0.7 | 99.3 | 52.5 | 52.2 | 99.0 |
| 5 | 0.9 | 0.5 | 51.8 | 0.0 | 0.6 | 0.6 | 99.4 | 52.6 | 52.3 | 98.9 |
| 6[a] | 1.0 | 0.9 | 54.2 | 0.6 | 2.9 | 0.4 | 99.0 | 57.6 | 57.1 | 95.0 |

[a]in the high boiler solution, EMIM $CH_3SO_3$ rather than EMIM Cl was used

Explanation:

Entries 1 & 2: The reaction can also be performed with glucose and gives good yields of HMF in the distillate. Compared to fructose (table 4), the reaction with glucose is somewhat less selective and leads to an increased extent of unwanted side reactions if the HMF formed cannot be removed quickly enough from the reaction solution.

Entry 3: At a lower reaction temperature of 180° C., the selectivity for HMF rises, but the distillation separation performance falls at the same time.

Entries 4 & 5: The reaction with a mixture of glucose and fructose leads to similarly good yields of HMF to those with pure glucose.

Entry 6: The reaction can be performed with equal yields also with EMIM $CH_3SO_3$.

The invention claimed is:

1. A process for preparing 5-hydroxymethylfurfural (HMF), which comprises
    a) feeding a starting solution comprising
        at least one hexose and
        a high boiler comprising an organic solvent having a boiling point greater than 200° C. (at standard pressure) and
        water,
        and low boiler comprising a solvent having a boiling point greater than 60° C. and less than 200° C. (at standard pressure) to a reaction vessel,
    b) converting hexose to HMF in the reaction vessel in the presence of the low boiler with simultaneous distillative removal of the HMF and
    c) obtaining, as a distillate, an aqueous, HMF-comprising solution.

2. The process according to claim 1, wherein the at least one hexose is fructose, glucose or mixtures of fructose and glucose.

3. The process according to claim 1, wherein the high boiler is a polyether or an ionic liquid.

4. The process according to claim 3, wherein the ionic liquid comprises imidazolium chlorides or imidazolium methanesulfonates.

5. The process according to claim 1, wherein the starting solution is prepared by the following steps:
    A1) the at least one hexose and water are present in a reaction vessel,
    A2) a further reaction vessel is initially charged with the high boiler and preferably a catalyst,
    A3) immediately prior to process step b), the components are mixed, optionally in a mixing chamber,
    the solutions of steps A1 and A2 being preheated to a temperature between 150 and 200° C. in the two reaction vessels separated from one another prior to the mixing.

6. The process according to claim 1, wherein the low boiler is water vapor, methanol or 2-butanol.

7. The process according to claim 1, wherein the starting solution comprises the high boiler in amounts of 5 to 90% by weight.

8. The process according to claim 1, wherein the starting solution comprises a metal chloride or metal nitrate of the formula $MX_n$ where M is a metal, X is chlorine or nitrate and n is an integer from 1 to 4.

9. The process according to claim 1, wherein the conversion to HMF is effected in the presence of an acid soluble in the starting solution.

10. The process according to claim 1, wherein the conversion to HMF is effected at a temperature from 100° C. to 250° C.

11. The process according to claim 1, wherein the conversion to HMF is effected at a pressure of 10 to 200 mbar.

12. The process according to claim 1, which is performed continuously, the starting solution and the low boiler being supplied continuously to the evaporator and the product solution being removed continuously.

13. The process according to claim 1, wherein the reaction vessel is a thin-film evaporator or a stripping column.

14. The process according to claim 1, wherein the low boiler is supplied in countercurrent to the starting solution.

15. The process according to claim 1, wherein more than 60% of the HMF obtained is present in the distillate.

16. The process according to claim 1, wherein the distillate is used for preparation of 2,5-furandicarboxylic acid or 2,5-bis(hydroxymethyl)furan.

17. The process according to claim 1, wherein the ionic liquid comprises 1-ethyl-3-methylimidazolium chloride (EMIM Cl), 1-butyl-3-methylimidazolium chloride (BMIM Cl), 1-ethyl-3-methylimidazolium methanesulfonate (EMIM CH3SO3) or 1-butyl-3-methylimidazolium methanesulfonate (BEMIM CH3SO3) or mixtures thereof.

18. The process according to claim 1, wherein at least 60% of the at least one saccharide hexose is converted to I-IMF in the process.

19. The process according to claim 1, wherein the ratio of the amount of low boiler supplied to the amount of the starting solution supplied is from 0.2:1 to 4:1.

20. The process according to claim 1, wherein in step b) the starting solution is contacted with the low boiler under reduced pressure.

21. The process according to claim 1, further comprising:
    d) discharging the low boiler and the volatile constituents of the starting solution via a separator at the top of the evaporator; and
    e) condensing the low boiler and the volatile constituents to from the distillate.

22. The process according to claim 1 comprising as step b) converting hexose to HMF in the reaction vessel in the presence of water vapor with simultaneous distillative removal of the HMF.

* * * * *